(12) United States Patent
Knebel et al.

(10) Patent No.: US 8,512,652 B2
(45) Date of Patent: *Aug. 20, 2013

(54) MULTIWELL MICROPLATE WITH TRANSPARENT BOTTOM HAVING A THICKNESS LESS THAN 200 MICROMETERS

(75) Inventors: Günther Knebel, Nurtingen (DE); Martin Bechem, Wuppertal (DE); Werner Stürmer, Wahlwies (DE); Ralph Noll, Haan (DE)

(73) Assignee: Greiner Bio-One GmbH, Frickenhausen (DE)

( * ) Notice: Subject to any disclaimer, the term of this patent is extended or adjusted under 35 U.S.C. 154(b) by 1006 days.

This patent is subject to a terminal disclaimer.

(21) Appl. No.: 10/271,232

(22) Filed: Oct. 15, 2002

(65) Prior Publication Data

US 2003/0039592 A1    Feb. 27, 2003

Related U.S. Application Data

(63) Continuation of application No. 08/899,405, filed on Jul. 23, 1997, now Pat. No. 6,514,464.

(30) Foreign Application Priority Data

Mar. 25, 1997  (DE) .................................. 197 12 484

(51) Int. Cl.
*B01L 3/00*   (2006.01)

(52) U.S. Cl.
USPC ............................ 422/553; 356/246; 422/552

(58) Field of Classification Search
USPC ......... 436/164, 165, 172; 422/102, 552–553; 356/246, 440; 435/288.3–288.4
See application file for complete search history.

(56) References Cited

U.S. PATENT DOCUMENTS

| | | | | |
|---|---|---|---|---|
| 4,004,150 | A | * | 1/1977 | Natelson ........................ 250/328 |
| 4,218,959 | A | * | 8/1980 | Numaguchi et al. ...... 92/103 SD |
| 4,493,815 | A | * | 1/1985 | Fernwood et al. ............ 422/101 |
| 4,498,780 | A | * | 2/1985 | Banno et al. .................. 356/414 |
| 4,662,360 | A | * | 5/1987 | O'Hara et al. ................. 600/200 |
| 4,680,655 | A | | 7/1987 | Sugawara |
| 4,704,255 | A | * | 11/1987 | Jolley .......................... 422/101 |
| 4,725,388 | A | | 2/1988 | Nelson |
| 4,734,192 | A | * | 3/1988 | Champion et al. ............ 210/335 |
| 4,735,778 | A | | 4/1988 | Maruyama et al. |

(Continued)

FOREIGN PATENT DOCUMENTS

| | | |
|---|---|---|
| DE | 2733214 A1 | 6/1978 |
| DE | 4217868 A1 | 12/1993 |

(Continued)

OTHER PUBLICATIONS

Assay Plate (1536 wells), D15, p1.

(Continued)

*Primary Examiner* — Arlen Soderquist
(74) *Attorney, Agent, or Firm* — Vista IP Law Group LLP

(57) ABSTRACT

The present invention relates to an improved microplate which is constructed of at least one frame part and at least one bottom part, where the bottom part has a maximum thickness of 500 μm.

26 Claims, 7 Drawing Sheets

(56) References Cited

U.S. PATENT DOCUMENTS

Figure 1:
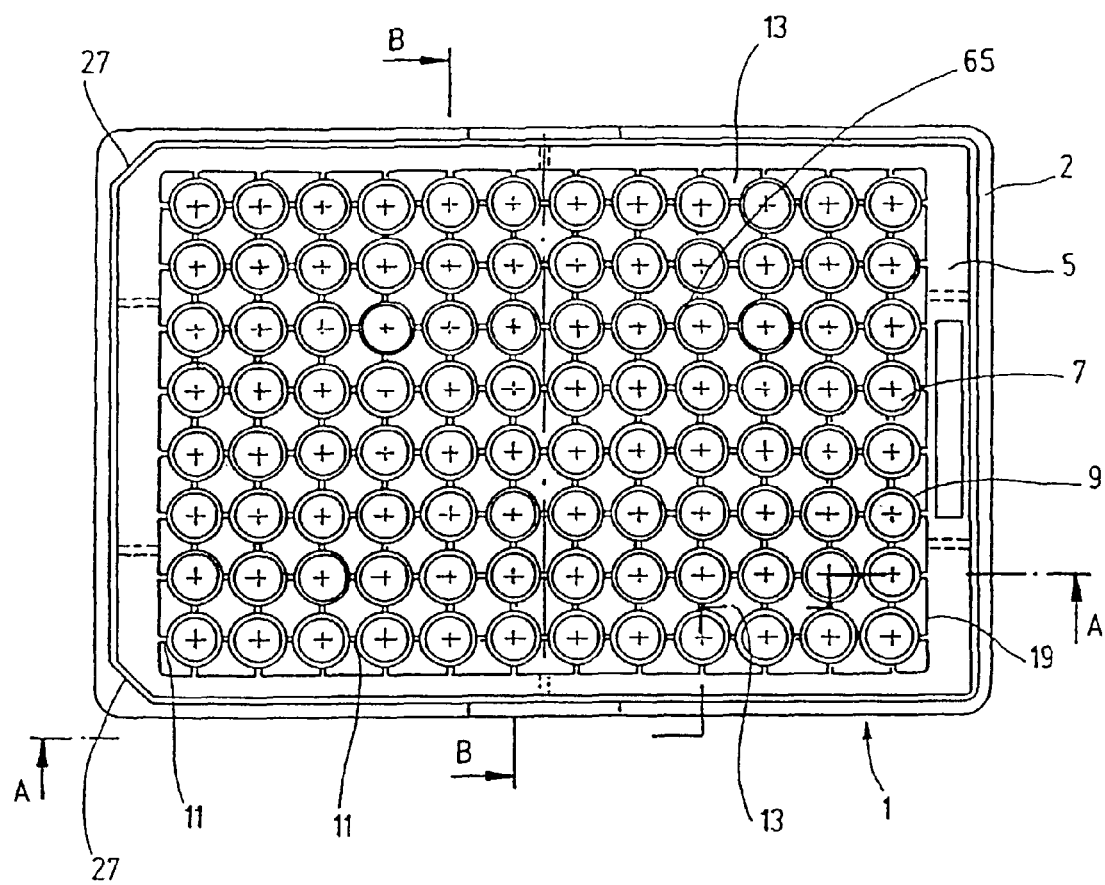

| | | | | |
|---|---|---|---|---|
| 4,948,442 | A | * | 8/1990 | Manns .................. 156/73.1 |
| 4,980,299 | A | * | 12/1990 | Batz et al. .................. 436/531 |
| 5,047,215 | A | | 9/1991 | Manns |
| 5,298,753 | A | * | 3/1994 | Sonne et al. .................. 250/364 |
| 5,319,436 | A | * | 6/1994 | Manns et al. .................. 356/246 |
| 5,417,923 | A | * | 5/1995 | Bojanic et al. .................. 422/101 |
| 5,459,300 | A | * | 10/1995 | Kasman .................. 219/433 |
| 5,487,872 | A | * | 1/1996 | Hafeman et al. .................. 422/102 |
| 5,508,197 | A | * | 4/1996 | Hansen et al. .................. 435/285.1 |
| 5,540,889 | A | | 7/1996 | Gordon et al. |
| 5,540,891 | A | | 7/1996 | Portmann et al. |
| 5,556,541 | A | * | 9/1996 | Ruschke .................. 210/232 |
| 5,679,310 | A | * | 10/1997 | Manns .................. 422/102 |
| 5,840,256 | A | * | 11/1998 | Demers et al. .................. 422/102 |
| 5,858,309 | A | | 1/1999 | Mathus et al. |
| 5,885,499 | A | * | 3/1999 | Aksberg .................. 264/153 |
| 5,989,854 | A | | 11/1999 | Cook |
| 6,051,191 | A | | 4/2000 | Ireland |
| 6,063,338 | A | * | 5/2000 | Pham et al. .................. 422/61 |
| 6,391,241 | B1 | * | 5/2002 | Cote et al. .................. 264/153 |
| 6,503,456 | B1 | | 1/2003 | Knebel .................. 422/102 |
| 6,514,464 | B1 | * | 2/2003 | Knebel .................. 422/102 |

FOREIGN PATENT DOCUMENTS

| | | | |
|---|---|---|---|
| DE | 9409089 | U1 | 12/1994 |
| EP | 131934 | * | 1/1985 |
| EP | 0408940 | A1 | 1/1991 |
| EP | 542422 | * | 5/1993 |
| EP | 0571661 | A1 | 12/1993 |
| EP | 0723812 | A1 | 7/1996 |
| EP | 0797088 | A1 | 5/2000 |
| GB | 1585768 | A | 3/1981 |
| GB | 2188418 | * | 9/1987 |
| JP | 59132335 | A | 7/1984 |
| JP | 61126450 | U | 8/1986 |
| JP | 7190924 | A | 7/1995 |
| JP | 8129014 | A | 5/1996 |
| JP | 8196299 | A | 8/1996 |
| WO | WO 94/08716 | * | 4/1994 |
| WO | WO 9503538 | A1 | 2/1995 |
| WO | WO 9517253 | A1 | 6/1995 |
| WO | 97/06890 | * | 2/1997 |

OTHER PUBLICATIONS

Ferragano, T. et al., Letter to the Editor, The Importance of Microplate Standardization, Journal of Biomolecular Screening, vol. 4, No. 4, 1999, 175.

Working Group Updates, Standards in Robotics and Intrumentation, Journal of Biomolecular Screening, vol. 1, Nov. 4, 1996 (6pp), No. 4, 1996, 163-168.

Greiner America, Inc., D16, pp. 1-8 (Oct. 1997).

Knebel, G., High Density Plates: 384 Wells—What is Next?, Greiner Labortechnik, MipTec '97, Washington, Jun. 1997, D14, pp. 1-5.

Knebel, G., 1536 Wells: New Developments in Plate Miniaturization (88), Greiner GmbH, Division, Labortechnik Development, D18, Jan. 21, 1998 (1p).

Knebel, G. et al., 1536 Wells: New Developments in Plate Miniaturization (88), LabAutmoation '98 Final Conference Program, Jan. 17-21, 1998, San Diego, CA, USA, D19, pp. 1-2.

Corning Costar Brochure: "The 96 well UV-plate TM" (1996) (2pp).

* cited by examiner

MULTIWELL MICROPLATE WITH TRANSPARENT BOTTOM HAVING A THICKNESS LESS THAN 200 MICROMETERS

This is a continuation of U.S. patent application Ser. No. 08/899,405, filed Jul. 23, 1997, now U.S. Pat. No. 6,514,464, which claims priority to German Patent Application No. 197 12 484. filed Mar. 25, 1997, now German Patent No. DE 197 12 484 C2. U.S. patent application Ser. No. 08/899,405 is expressly incorporated by reference herein in its entirety. Priority to each of the aforementioned applications is hereby expressly claimed in accordance with 35 U.S.C. Section. 365.35 U.S.C. Section 120 and any other applicable statutes.

The invention relates to a microplate with transparent bottom as well as to a method for its manufacture.

Microplates are known which are used for fluorescence, luminescence or scintillation measurements, for example, in solving biochemical or molecular biological questions.

New luminescence and fluorescence techniques require the preparation of colored microplates with transparent bottoms. Microplates with 96 wells today represent a standardized platform for automatic or manual determination, and for evaluation of patient specimens in widespread analysis equipment. A routine method for the preparation of colored microplates with transparent bottoms is ultrasound welding of a colored plate frame to a transparent bottom. It is preferable that both parts be made of polystyrene. Achieving an absolute seal between the 96 wells always turns out to be a problem. Therefore, double welding beads are frequently applied to achieve a greater level of safety.

EP-0,571,661 A1 discloses a microplate which is used in measurement techniques where the light emission or light permeability is measured. The disclosed microplate compresses a cuvette-forming upper light-impermeable frame part as well as a light-permeable bottom part, which is attached by means of ultrasound welding to the upper frame part. There are also known variants of these microplates in which, below the transparent bottom part, a protective grid is applied which is made of nontransparent material, and which leaves clear the optical window. Manufacture of such microplates may employ multicomponent injection molding processes, where, by means of two injection molds, the frame and bottom parts are manufactured and assembled.

The drawback of the known microplates is that the transparent bottom parts, because of their thickness of approximately 1 mm, present light conduction effects which are the result of the deflection and total reflection of light. Total reflection occurs whenever light moves through an interface between an optically denser medium and an optically less dense medium, and the limiting angle, which is specific for the material, is exceeded. This property is used to good effect today in light conduction technology. Light is fed into one end of a light conductor, then exits through the other end, practically unweakened because of the total reflection. To achieve this effect, the walls of the fibers must, however, be absolutely smooth at optical dimensions. If this is not the case, as in injection molded part, then the reflection of the light is not total, only partial, and therefore it can exit through adjacent wells, or cuvettes. The adverse light conduction effect also occurs, for example, during transmitted light measurements, and its characteristics include the fact that the transparent bottom acts as a light conductor and, for given cuvettes, deflects incident light partially into adjacent cuvettes. In this context, it has been observed that, as the thickness of the bottom increases, the light conduction effect also increases, that is, the measurement accuracy decreases. In addition, the known microplates are only suited under certain conditions for radioactivity measurements, for example, scintillation measurements, also because of the thickness of their transparent bottoms.

The technical problem which is the foundation of the present invention thus consists in preparing microplates which overcome the above-mentioned drawbacks, particularly which guarantee a higher accuracy during optical measurements and, moreover, are also suited-for radioactive determinations.

The invention solves this problem by the preparation of a microplate with the characteristics of the main claim, particularly by the preparation of a microplate with at least one frame part and at least one bottom part associated with the frame part, where the frame part, of which there is at least one, comprises multiple cuvettes and the bottom part, of which there is at least one, forms the bottoms of the cuvettes, and where the bottom part, respectively the bottoms, of the cuvettes has/have a maximum thickness of 500 µm, preferably 20-500 µm, and optimally 40 to 100 µm.

In connection with the present invention, the term frame part of a microplate is understood to refer to that part of a microplate which forms the cuvettes or recesses, in particular their lateral walls, which are open towards both the top and bottom. The term bottom part of a microplate is understood to refer to that part of a microplate which closes off the cuvettes, and optionally the cuvette interstices, towards the bottom.

In connection with the present invention, the term cuvette is understood to refer to a container which can be made of any material, preferably plastic, and which is in the form of a cupule, well, bore, hollowed-out part or similar configuration, and which is used for receiving the samples to be examined. In a particularly preferred manner, the entire bottom part, or only those parts of the bottom part which form the bottoms of the cuvette, are made in the form of a membrane or, particularly, a transparent film.

The invention thus makes available, in an advantageous manner, a microplate which provides, because of the very small thickness of the bottom part, respectively the bottoms of the cuvettes, multiple advantages and applications. Because of the small thickness of the bottom part, respectively the bottoms of the individual cuvettes, it is, for example, possible and particularly advantageous for use in radioactivity determinations. To the extent that the bottom part is in the form of a transparent film, the resulting advantage is that the undesired light conduction effect is considerably reduced, so that measurements can be carried out with considerably increased accuracy, compared to the state of the art. To the extent that the bottom part is in the form of a membrane, it is possible to carry out any desired nutrient diffusion from the bottom through the membrane into the cells that grow on the membrane in the cuvette in a particularly efficient manner, and to a large extent unimpeded.

The microplates according to the invention are therefore suited for any kind of fluorescence, luminescence, calorimetric, chemilumescence or radioactivity measurement, for example, scintillation measurements. The microplates according to the invention can be used in ELISA tests, DNA and RNA hybridizations, antibody titer determinations, protein, peptide and immuno tests, PCR and recombinant DNA techniques, hormone and receptor binding tests and similar techniques. Since it is preferable to use, for the bottom part, respectively the bottoms of the individual cuvettes, transparent, that is light-permeable, materials, optical apparatuses can be placed both above and below the microplate. In addition it is possible to study the samples contained in the cuvettes using light microscopy.

The microplate according to the invention presents at least a frame part and at least one bottom part associated with the frame part. The frame part, of which there is at least one, is preferably essentially in the form of a rectangle and it comprises multiple cuvettes which are open towards the top and towards the bottom, in a support plate, where the lateral walls of the cuvettes are formed by the frame part which in this area is in the form of a support plate. The cuvettes that are formed in the frame part can have a circular, hexagonal, square or other geometric cross section. The cuvettes are arranged in the support plate of the frame part in the form of a matrix or in rows. The cuvettes in the support plate can be in the form of distinct individual cuvettes, connected, for example, by connecting rods, in the form of bores in an otherwise solid support plate, or in the form of a combination of the two embodiments. Per frame part it is possible to have 6, 12, 24, 48, 96 or multiples thereof, for example, 384 or 1536, cuvettes. The frame part is applied in the injection molding process onto the bottom part which has a maximum thickness of 500 µm, which bottom part thus closes the cuvettes from the bottom and at the same time forms the bottom for each individual cuvette. The microplate according to the invention can consist, for example, of such a frame part and a bottom part associated with this frame part. However, it is also possible according to the invention to use a design where one or preferably more frame parts are arranged in the middle of a foundation frame, in a manner so that it/they can be removed. Such a microplate accordingly comprises a foundation frame and frame parts, each provided with a bottom part, which are arranged in the foundation frame.

In another preferred embodiment, the invention provides for the coloring of the frame part, either black or white, or in natural, transparent, colors. In a particularly preferred manner, the frame part is manufactured of one material type or of a mixture of materials, guaranteeing an increased heat conductivity, for example, by the inclusion of metal shavings, such as shavings of nickel, special steel, or rust.

In a particularly advantageous embodiment, the invention provides for manufacturing the frame part of acrylbutadienestyrene (ABS), polyamide (PA), polycarbonate (PC), polystyrene (PS), polymethyl methacrylate (PMMA), polypropylene (PP) or styrene acrylonitrile (SAN).

In an additional advantageous embodiment, the invention provides for manufacturing the film of a transparent material, or for coloring it. According to the invention it is possible to use a film with increased heat conductivity, for example, by using aluminum as film material. In a particularly preferred embodiment of the present invention, the film is constructed in several layers, where, for example, the face of the film turned toward the frame part is chosen so that it provides for a particularly good connection to the frame part, whereas the face of the film turned away from the frame part is used to improve the stability.

It is particularly preferred for the film to be made of acrylobutadienestyrene (ABS), polyamide (PA), polycarbonate (PC), polystyrene (PS), polymethyl methacrylate (PMMA), polypropylene (PP) or styrene acrylonitrile (SAN), and for it to consist of these materials or mixtures thereof.

In a particularly preferred embodiment, the membranes according to the invention are manufactured of the polyamide (PA6, PA66), polyester (PET, PETG), polycarbonate (PC), cellulose, cellulose derivative or regenerated cellulose, and they consist of these materials or mixtures thereof.

Preferably the invention provides for a constant thickness of the bottom part and for the bottom part to be made in its entirety of the same material. However, the invention also provides for the bottom part to have a maximum thickness of 500 µm only in those areas in which the bottom part forms the bottom of the respective cuvette, whereas in the areas between the cuvette bottoms and/or in the areas below the cuvette lateral walls a larger thickness of the bottom part is provided and/or another material composition.

The invention, in an additional advantageous embodiment, provides for a support structure below the bottom part which is used for stabilizing the bottom part and which is attached by welding or applied by spraying onto the bottom part or onto the frame part itself. Advantageously, this support structure leaves an optical window free, in each case under the cuvette bottom.

Furthermore, the invention provides for a notching or other marking of at least one, preferably two, corners of the frame part or of the foundation frame, so that an equivocal orientation can be used.

The invention also relates to another method for the manufacture of microplates consisting of at least one frame part and at least one bottom part, where the bottom part has a maximum thickness of 500 µm. The invention provides for the manufacture of the microplates according to the invention in a single-step procedure, where the bottom part, which is in the form of a film or membrane, is arranged in an injection molding installation and subsequently a molding composition, heated at 200-300° C., preferably 250° C., and plasticized, is injected for the manufacture of the frame part into the injection molding installation and applied to the bottom part.

The method according to the invention provides for a thin, prestamped, film or membrane, having preferably a thickness of 60 µm, which is inserted into an injection molding mold, and around which is sprayed the material used for the frame part and connected to it. The material can be transparent, or colored with a white or black with high covering power. The fixation of the film or membrane can be carried out using a vacuum through small channel slits, which, however, do not leave any visible imprints on the mold part, or by electrostatic charging of the film, or the membrane and/or injection molding tool.

Using this method, it is possible, for example, to use the application process by spraying around films or membranes made of polymethyl methacrylate, polyester, or polycarbonate, and having a thickness range of 20-500 µm. According to the invention, it should be considered preferable to obtain a good connection between the film or membrane and the mold composition sprayed around it. Optionally, the film or membrane according to the invention can be subjected to a preliminary treatment using the corona or plasma processes respectively, preactivated with appropriate adhesives. The temperature resistance of the composite is a function of the film or membrane and of the mold composition used for the manufacture of the frame part and it is, for example, in the case of polystyrene approximately 50° C. It is preferable to ensure that no thermal deformation of the film or membrane occurs, when the heated mold composition (approximately 250° C.) is injected. The injection molding tool should be designed in such a manner that the film or membrane is not shifted.

Using appropriate films or membranes, it is possible to use this processing technique to achieve a great number of different objectives. The objectives include improved properties of use, such as high light permeability and good resistance to chemicals. Furthermore, according to the invention it is possible to render the film surfaces hydrophilic or hydrophobic by plasma or corona processes, and to incorporate functional amino groups. Microplates modified according to the invention can be used in immunoassays and cell cultivation. According to the invention, it is also possible to apply sprays around the membranes which are to be used for cell culture techniques and filtration processes.

A sterilization which may be required with accelerated electrons or gamma quanta does not lead to any noteworthy changes in the materials.

The use of an adapted tool makes it possible to manufacture in small or large series with a good cost-benefit ratio. Without long interruption of production, it is thus possible to manufacture different qualities of films or surfaces.

Other advantageous embodiments of the invention can be obtained from the secondary claims.

The invention is further explained with reference to the embodiment examples and the associated figures.

Figure 2:
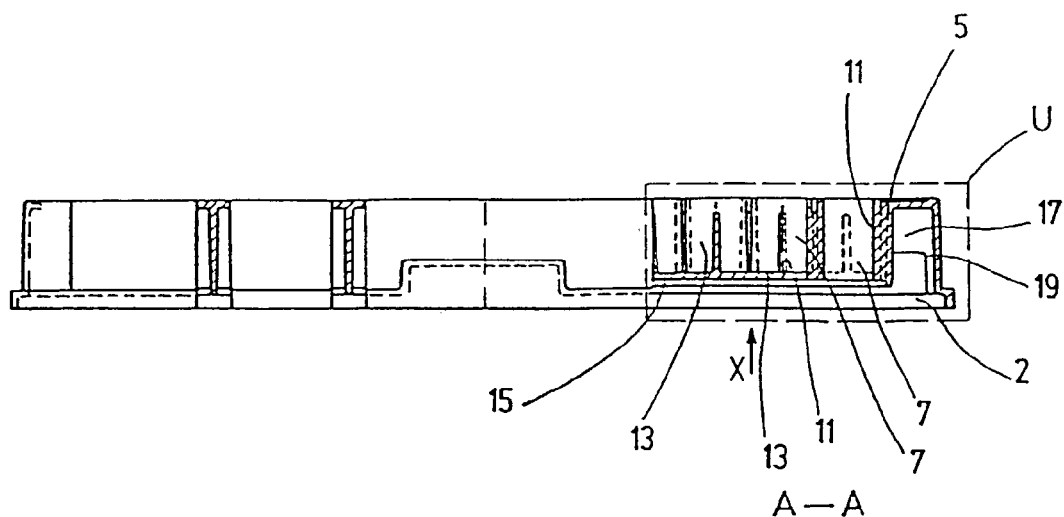
Figure 3:
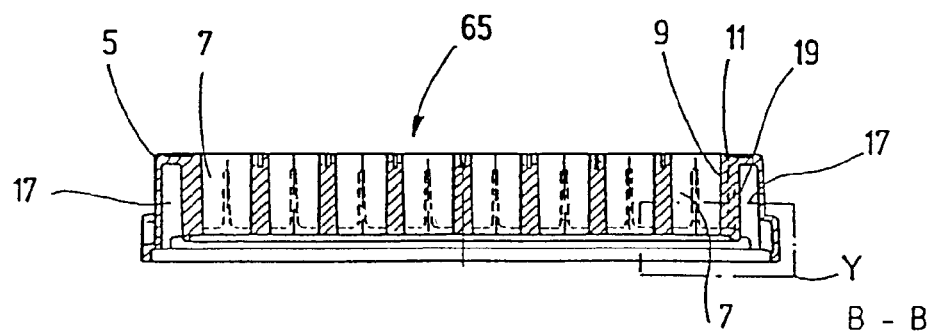
Figure 4:
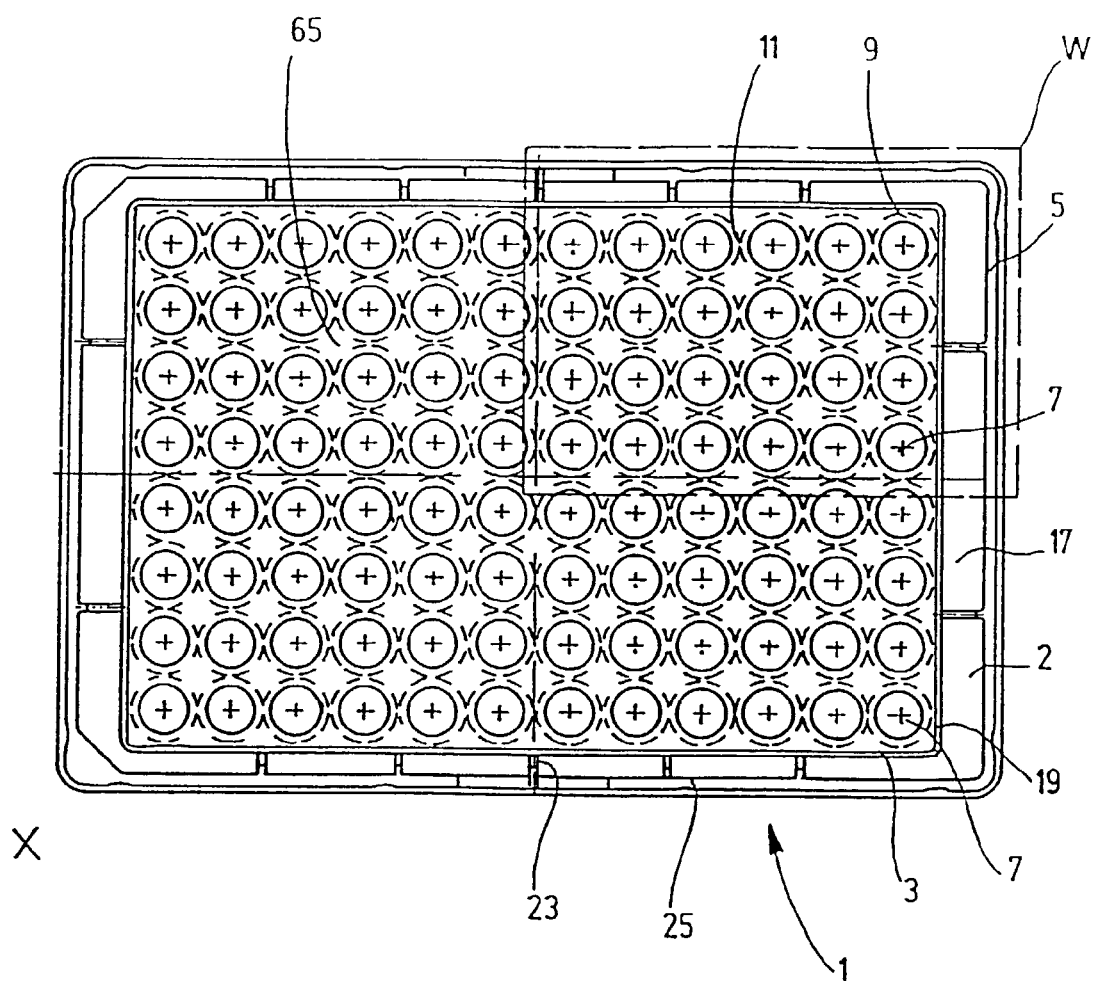

The figures show:

FIG. 1: A top view onto the microplate according to the invention,

FIG. 2: A shifted cross section through the microplate of FIG. 1,

FIG. 3: An additional cross section through the microplate of FIG. 1,

FIG. 4: A bottom view of the bottom part of the microplate according to FIG. 1, FIG. 5: A detail of FIG. 4, FIG. 6: A detail of the cross-sectional representation of FIG. 2, FIG. 7: A detail of FIG. 6, and FIG. 8: An alternate embodiment form of the invention with frame parts arranged in a foundation frame.

FIG. 1 shows a microplate 1 with a rectangular frame part 2, which has rounded corners, made of a white polystyrene, which is colored so it has covering power, and a bottom part 3 arranged with it [frame part 2], and not represented here. Frame part 2 is manufactured as a single part, and it presents the standard dimensions of the SBS (Society of Biomolecular Screening) standard (MIPTEC standardization draft of Oct. 12, 1996) and it presents a support plate 5, which is formed in the cuvette 7 in the form of an 8×12 matrix. The cuvettes 7 which are circular in cross section are open towards the top, and their lateral walls 9 are formed by the support plate 5. The lateral cuvette walls 9 are connected to the respective adjacent lateral cuvette walls, or the interior frame wall 19 of the frame part 2, by means of stays 11. Between the lateral walls 9 of the cuvettes 7, interstices 13 are therefore arranged. These interstices 13 are open towards the top, whereas they are closed towards the bottom by a closing plate 15 (FIG. 2). The frame part 2 presents two notched corners 27. The individual cuvettes 7 can be identified by means of alphanumerical and numerical markings on the matrix.

Figure 6:
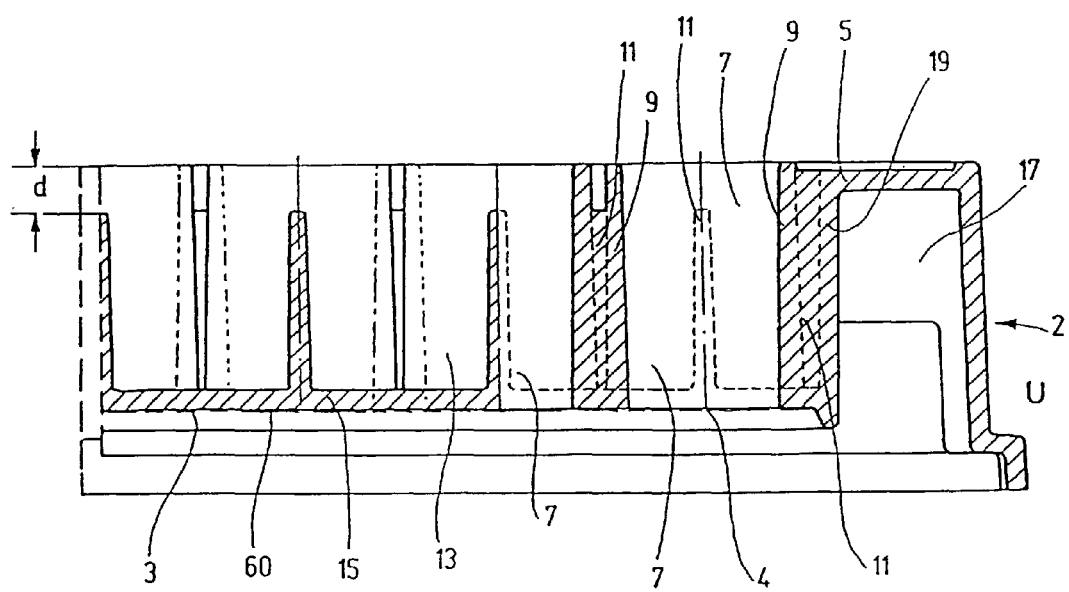

FIG. 2 represents a shifted cross section through the microplate according to FIG. 1. FIG. 6 is a detail of FIG. 2. One can see that the microplate 1 presents, in its marginal area over the entire circumference, a hollow wall 17, which is open towards the bottom, and formed by the support plate 5. The cuvettes 7 which present lateral walls 9 formed by the support plate 5, are each connected by means of four stays 11, which form a 90° angle between each other, with the adjacent cuvettes 7 or the interior frame wall 19. The interior frame wall 19 thus forms, in a manner of speaking, the interior inside wall, turned towards the cuvette area, of the hollow wall 17, and it comprises the entire cuvette area 65. Furthermore, one can see the interstices 13 which are opened towards the top and which are closed towards the bottom by the closing plate 15 formed by the support plate 5. The closing plate 15 only closes the interstices 13 located between the cuvettes 7, in the direction of the bottom, and not the cuvettes 7 themselves. FIGS. 2 and 6 also show that the stays 11 do not reach the height of the cuvettes 7 completely, rather they end at a separation d below the upper edge of the cuvettes 7. Naturally it is also possible, depending on the geometry of the cuvettes, to omit the use of the stays, interstices, closing plates and/or interior frame wall.

FIG. 6 clearly shows that both the cuvettes 7 which are open towards the bottom and the closing plate 15 are covered by a film 3. The film 3 presents a constant thickness of 60 μm and it is made of polystyrene. The passage of light is not prevented over the entire internal diameter of the cuvettes 7. The film 3 forms the bottoms 4 of the cuvettes 7 and it covers the closing plate 15 in the areas 60.

Figure 7:
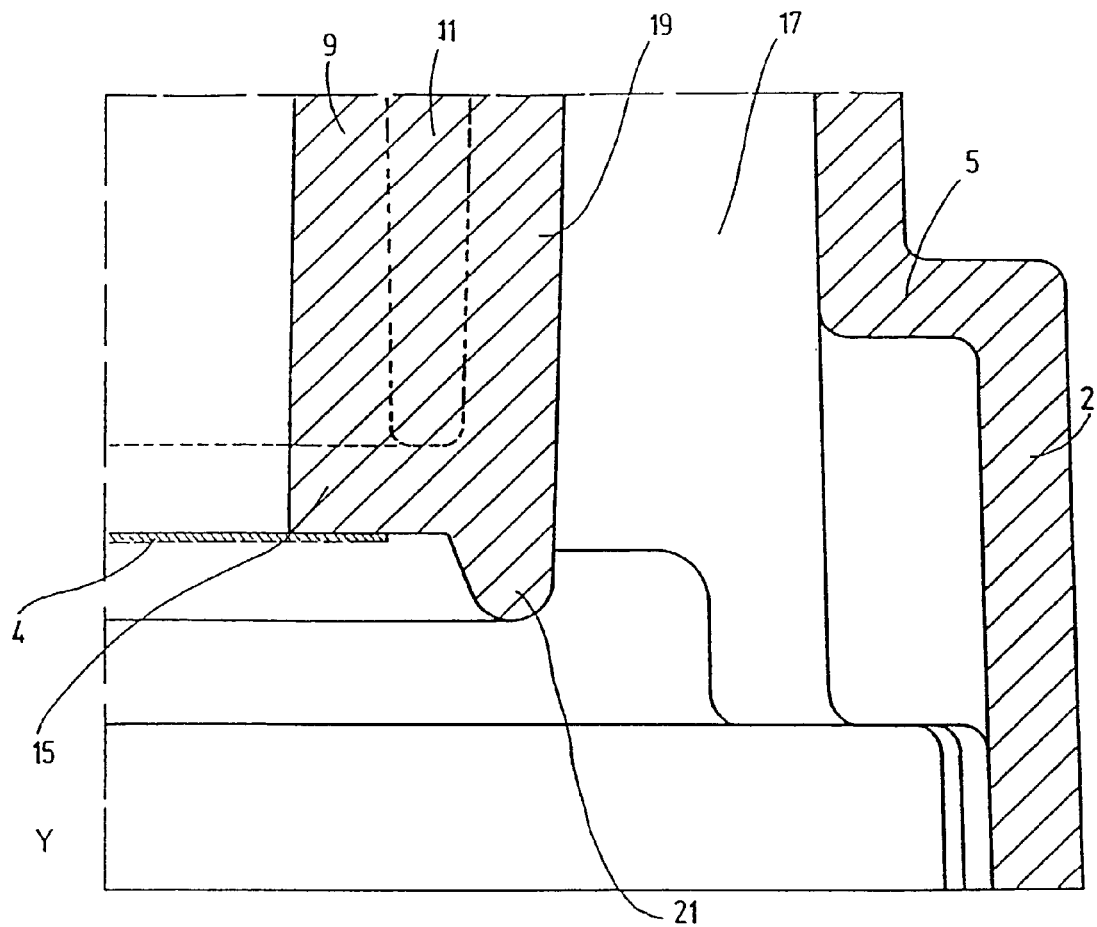

FIG. 3 represents a shifted cross section, which is diagonal with respect to the longitudinal axis of the microplate according to FIG. 1. FIG. 7 is a detail view of FIG. 3. In both figures it is also possible to see the hollow wall 17, which covers the entire circumference of the microplate 1, and is open towards the bottom and formed by the support plate 5. Furthermore, the representation includes the interior frame wall 19 which surrounds the cuvette area 65, the stays 11 which connect the cuvettes 7, and the lateral walls 9 of the cuvettes 7. FIG. 7 shows, in detail, a lower corner area of the microplate 1 shown in FIG. 3. The representation shows the hollow wall 17 which is made of the support plate 5 of the frame part 2, with its interior frame wall 19 and the stay 11 and the lateral wall 9 of the cuvette 7. The interior frame wall 19, which encloses the entire cuvette area 65 can be clearly seen, and projecting beyond the level of the closing plate 15 towards the bottom with projection 21. Furthermore, the bottom part 3, which is in the form of a film, is also shown, and which covers without gap, the entire cuvette area 65 towards the bottom. Both the closing plate 15 and the cuvettes 7 open towards the bottom, and are covered by the film, so that the cuvettes present a flat bottom 4.

FIG. 4 is a view of the microplate 1 from the bottom. The representation shows the hollow wall 17 formed by the support plate 5 of the frame part 2, with its interior frame wall 19. The representation also shows connecting stays 23 between the interior frame wall 19 and the frame exterior wall 25 of the frame part 2. It is possible to recognize the cuvettes 7, which are covered towards the bottom by the transparent bottom part 3, in the form of a film, and the cuvettes' lateral wall 9 as well as the stays 11. Furthermore, one can also see that the closing plate 15, which closes off the interstices 13 toward the bottom, is covered by the bottom part 3.

Figure 5:
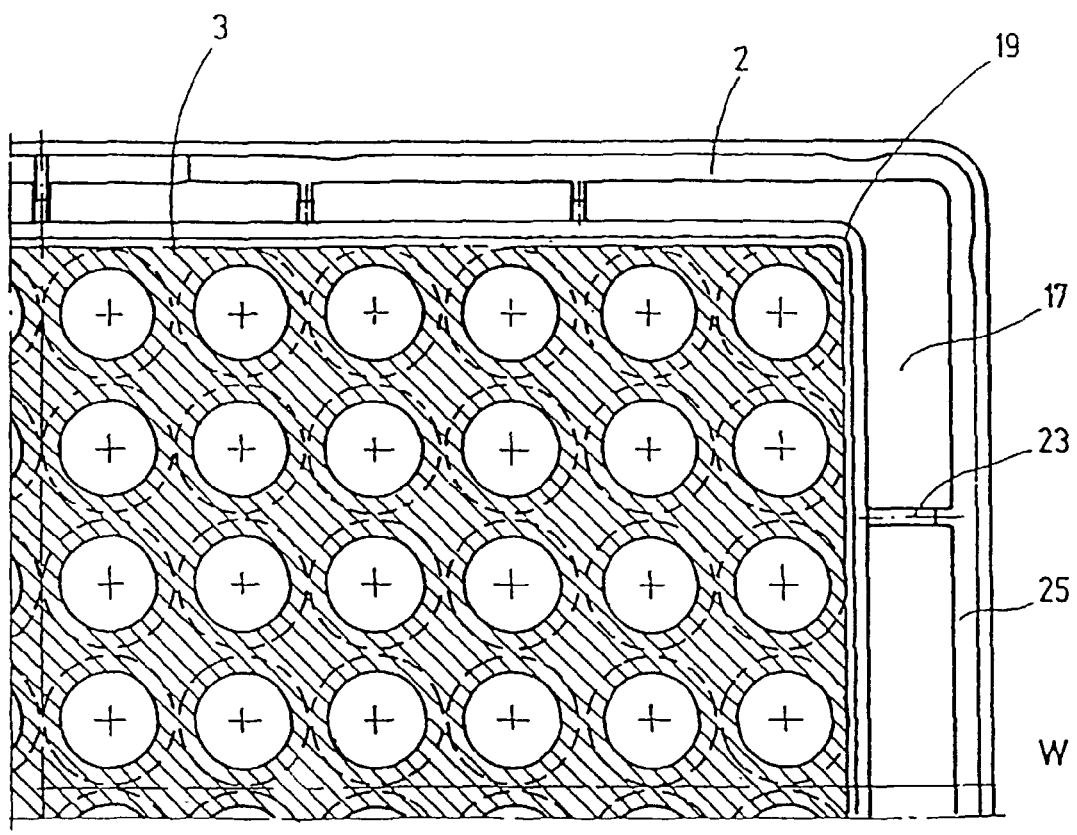

FIG. 5 represents a detailed view of FIG. 4 and makes it clear that the bottom part 3 closes off the entire cuvette area 65 of the frame part 2 towards the bottom.

Figure 8:
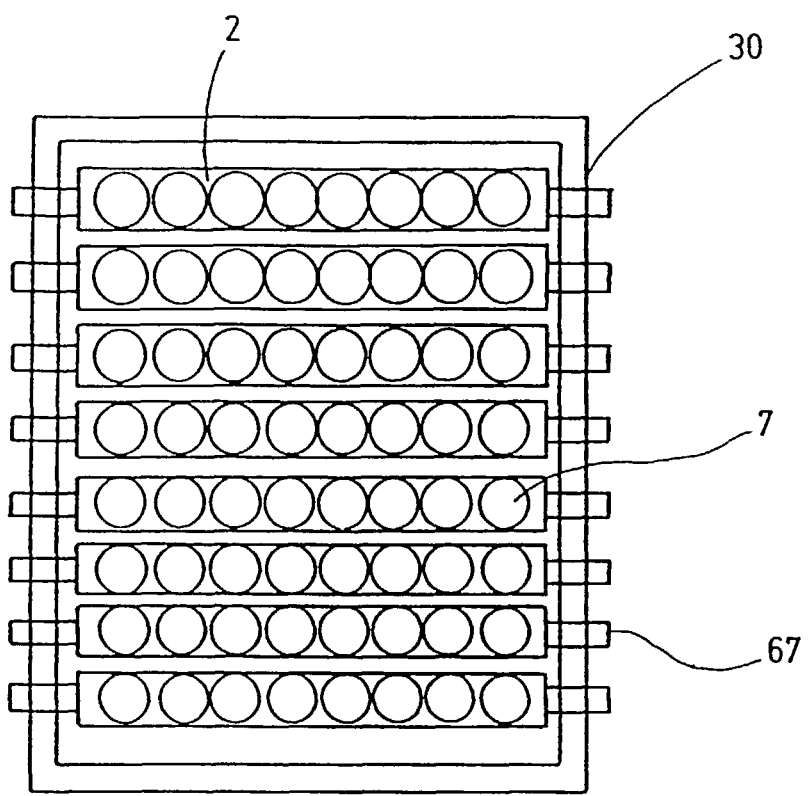

FIG. 8 represents an additional embodiment of the invention. In foundation frame 30, which is opened in its middle towards the bottom, eight units are arranged in such a manner that they can be taken out using the gripping surfaces 67, each unit being made of a frame part 2 and bottom part 3 which presents eight cuvettes in the form of a strip.

The manufacture of the microplate 1 took place as follows. A transparent polystyrene film with a thickness of 60 μm is positioned in an injection molding tool. The arrangement occurs in a manner such that the molding composition to be injected by spraying cannot spray under the film, and access to the spraying space is prevented for larger dust particles. For the manufacture of the frame part 2, white colored polystyrene is used. The polystyrene was first heated at 260° C. in a cylinder and thus converted to its plastic state. The plasticized molding composition was then pressed by means of a conveyor belt at a pressure of 1000 bar out of the cylinder, and rapidly injected into the cooled closed tool in which the film was positioned. The mold part sets with a post-pressure application of approximately 250 bar, and shrinkage of the cooling mold part was compensated for by the addition of pressurized plastic composition. The post-pressure application time until setting was a few seconds, but can be several minutes in the case of larger parts with thick walls. After the cooling and the rigidification, the mold part applied to the film is ejected.

The invention claimed is:

1. A microplate for use in analysis of samples, the microplate comprising:
an injection molded plastic frame;
96 or more injection molded plastic sample cuvettes, each sample cuvette having a side portion and a bottom portion, each cuvette being arrayed in the frame; and
a non-porous, transparent film forming the bottom of each cuvette, the frame and cuvettes injection molded onto said film at a temperature and pressure which is effective for attachment of the film onto each cuvette, the film having a thickness of less than about 200 μm, wherein the film forming the bottom of each cuvette forms a fluid tight seal to the side portion of such cuvette along the entire perimeter of the bottom portion of each cuvette such that the bottom and side portion of each cuvette form a fluid tight chamber for containing the sample.

2. The microplate for use in analysis of samples as recited in claim 1 wherein the plastic for the cuvette and the frame being selected from the group consisting of acrylobutadienestyrene, polyamide, polycarbonate, polystyrene, polymethyl methacyrlate, polypropylene, styrene acrylonitirle and mixtures thereof, the film being selected from the group consisting of acrylobutadienestyrene, polyamide, polycarbonate, polystyrene, polymethyl methacrylate, polypropylene, styrene acrylonitirle, polyester, cellulose, cellulose derivatives, regenerated cellulose and mixtures thereof.

3. The microplate for use in analysis of samples as recited in claim 2 wherein the film is injected molded with the frame and cuvettes at a temperature in the range of from 200° C. to 300° C.

4. The microplate for use in analysis of samples as recited in claim 2 wherein the frame and the sides of the cuvettes further include at least one heat conducting material which will increase the heat conductivity of the frame and cuvettes over the heat conductivity of the frame and cuvettes without the heat conducting material.

5. The microplate for use in analysis of samples as recited in claim 1 wherein the film is injected molded with the frame and cuvettes at a temperature in the range of from 200° C. to 300° C.

6. A microplate for use in analysis of samples, the microplate comprising:
an injection molded plastic frame;
96 or more injection molded plastic sample cuvettes, each sample cuvette having a side portion and a bottom portion, each cuvette being arrayed in the frame; and
a transparent film forming the bottom of each cuvette, the frame and cuvettes injection molded onto said film at a temperature in the range of from 200° C. to 300° C. for attachment onto each cuvette, the film having a thickness of less than about 200 μm thick, wherein the film forming the bottom of each cuvette forms a fluid tight seal to the side portion of such cuvette along the entire perimeter of the bottom portion of each cuvette such that the bottom and side portion of each cuvette form a fluid tight chamber for containing the sample.

7. The microplate for use in analysis of samples as recited in claim 6 wherein the plastic for the cuvette and the frame being selected from the group consisting of acrylobutadienestyrene, polyamide, polycarbonate, polystyrene, polymethyl methacyrlate, polypropylene, styrene acrylonitirle and mixtures thereof, the film being selected from the group consisting of acrylobutadienestyrene, polyamide, polycarbonate, polystyrene, polymethyl methacrylate, polypropylene, styrene acrylonitirle, polyester, cellulose, cellulose derivatives, regenerated cellulose and mixtures thereof.

8. The microplate for use in analysis of samples as recited in claim 7 wherein the frame and the sides of the cuvettes further include at least one heat conducting material which will increase the heat conductivity of the frame and cuvettes over the heat conductivity of the frame and cuvettes without the heat conducting material.

9. The microplate for use in analysis of samples as recited in claim 6 wherein the frame and the sides of the cuvettes further include at least one heat conducting material which will increase the heat conductivity of the frame and cuvettes over the heat conductivity of the frame and cuvettes without the heat conducting material.

10. A microplate for use in analysis of samples, the microplate comprising:
an injection molded plastic frame;
384 or more injection molded plastic sample cuvettes, each sample cuvette having a side portion and a bottom portion, each cuvette being arrayed in the frame; and
a transparent film forming the bottom of each cuvette, the frame and cuvettes injection molded onto said film, the injection molding being at a temperature and pressure which is effective for attachment of the film onto each cuvette, the film having a thickness of less than about 200 μm, wherein the film forming the bottom of each cuvette forms a fluid tight seal to the side portion of such cuvette along the entire perimeter of the bottom portion of each cuvette such that the bottom and side portion of each cuvette form a fluid tight chamber for containing the sample.

11. The microplate for use in analysis of samples as recited in claim 10 wherein the plastic for the cuvette and the frame being selected from the group consisting of acrylobutadienestyrene, polyamide, polycarbonate, polystyrene, polymethyl methacyrlate, polypropylene, styrene acrylonitirle and mixtures thereof, the film being selected from the group consisting of acrylobutadienestyrene, polyamide, polycarbonate, polystyrene, polymethyl methacrylate, polypropylene, styrene acrylonitirle, polyester, cellulose, cellulose derivatives, regenerated cellulose and mixtures thereof.

12. The microplate for use in analysis of samples as recited in claim 11 wherein the film is injected molded with the frame and cuvettes at a temperature in the range of from 200° C. to 300° C.

13. The microplate for use in analysis of samples as recited in claim 10 wherein the film is injected molded with the frame and cuvettes at a temperature in the range of from 200° C. to 300° C.

14. The microplate for use in analysis of samples as recited in claim 10 wherein the frame and the sides of the cuvettes further include at least one heat conducting material which will increase the heat conductivity of the frame and cuvettes over the heat conductivity of the frame and cuvettes without the heat conducting material.

15. A microplate for use in analysis of samples, the microplate comprising:
an injection molded plastic frame;
384 or more injection molded plastic sample cuvettes, each sample cuvette having a side portion and a bottom portion, each cuvette being arrayed in the frame; and
a transparent film forming the bottom of each cuvette, the frame and cuvettes injection molded onto said film at a temperature and pressure which is effective for attachment of the film onto each cuvette, the film having a thickness of from about 40 to about 200 μm thick, the film forming the bottom of each cuvette forming a fluid tight seal to the side portion of such cuvette along the entire perimeter of the bottom portion of each cuvette such that the bottom and side portion of each cuvette form a fluid tight chamber for containing the sample, the plastic for the frame and the plastic for the cuvette being selected from the group consisting of acrylobutadienestyrene, polyamide, polycarbonate, polystyrene, polymethyl methacrylate, polypropylene, styrene acrylonitirle and mixtures thereof, the film being selected from the group consisting of acrylobutadienestyrene, polyamide, polycarbonate, polystyrene, polymethyl methacrylate, polypropylene, styrene acrylonitirle, polyester, cellulose, cellulose derivatives, regenerated cellulose and mixtures thereof.

16. The microplate for use in analysis of samples as recited in claim 15 wherein the film is injected molded with the frame and cuvettes at a temperature in the range of from 200° C. to 300° C.

17. The microplate for use in analysis of samples as recited in claim 16 wherein the frame and the sides of the cuvettes further include at least one heat conducting material which will increase the heat conductivity of the frame and cuvettes over the heat conductivity of the frame and cuvettes without the heat conducting material.

18. A microplate for use in analysis of samples, the microplate comprising:
an injection molded plastic frame;
384 or more injection molded plastic sample cuvettes, each sample cuvette having a side portion and a bottom portion, each cuvette being arrayed in the frame; and
a transparent film forming the bottom of each cuvette, the frame and cuvettes injection molded onto said film at a temperature in the range of from 200° C. to 300° C. and at a temperature and pressure which is effective for attachment of the film onto each cuvette, the film having a thickness of from about 40 to about 200 μm thick, wherein the film forming the bottom of each cuvette forms a fluid tight seal to the side portion of such cuvette along the entire perimeter of the bottom portion of each cuvette such that the bottom and side portion of each cuvette form a fluid tight chamber for containing the sample.

19. The microplate for use in analysis of samples as recited in claim 18 wherein the frame and the sides of the cuvettes further include at least one heat conducting material which will increase the heat conductivity of the frame and cuvettes over the heat conductivity of the frame and cuvettes without the heat conducting material.

20. A microplate as defined in claim 19, wherein the bottoms of the multiple sample cuvettes are of essentially constant thickness.

21. A microplate for use in analysis of samples, the microplate comprising:
an injection molded plastic frame having 96 or more sample cuvettes arrayed in the frame, each sample cuvette having a side portion and being open at its top and having an opening at its bottom; and
a transparent film having a thickness of less than about 500 μm attached to said frame, said film being attached to said frame by injection molding the frame onto said film at a temperature and pressure which is effective for attachment of said film onto said frame wherein said film forms a fluid tight seal over the opening of each cuvette.

22. The microplate for use in analysis of samples as recited in claim 21 wherein the plastic for the cuvette and the frame being selected from the group consisting of acrylobutadienestyrene, polyamide, polycarbonate, polystyrene, polymethyl methacyrlate, polypropylene, styrene acrylonitirle and mixtures thereof, the film being selected from the group consisting of acrylobutadienestyrene, polyamide, polycarbonate, polystyrene, polymethyl methacrylate, polypropylene, styrene acrylonitirle, polyester, cellulose, cellulose derivatives, regenerated cellulose and mixtures thereof.

23. The microplate for use in analysis of samples as recited in claim 22 wherein the film is injected molded with the frame and cuvettes at a temperature in the range of from 200° C. to 300° C.

24. The microplate for use in analysis of samples as recited in claim 22 wherein the frame and the sides of the cuvettes further include at least one heat conducting material which will increase the heat conductivity of the frame and cuvettes over the heat conductivity of the frame and cuvettes without the heat conducting material.

25. The microplate for use in analysis of samples as recited in claim 21 wherein the film is injected molded with the frame and cuvettes at a temperature in the range of from 200° C. to 300° C.

26. A microplate for use in analysis of samples, the microplate comprising:
an injection molded plastic frame;
96 or more injection molded plastic sample cuvettes, each sample cuvette having a side portion and a bottom portion, each cuvette being arrayed in the frame and said cuvettes being integrally formed with said plastic frame by injection molding; and
a transparent film forming the bottom of each cuvette, the frame and cuvettes injection molded onto said film at a temperature and pressure which is effective for attachment of the film onto each cuvette, the film having a thickness of less than about 200 μm, wherein the film forming the bottom of each cuvette forms a fluid tight seal to the side portion of such cuvette along the entire perimeter of the bottom portion of each cuvette such that the bottom and side portion of each cuvette form a fluid tight chamber for containing the sample.

* * * * *